United States Patent
Jorgensen et al.

(10) Patent No.: US 6,592,507 B2
(45) Date of Patent: *Jul. 15, 2003

(54) PLATELET COLLECTION SYSTEM

(75) Inventors: Glen E. Jorgensen, Marlboro, MA (US); Bruce Berckmans, III, Palm Beach Gardens, FL (US)

(73) Assignee: Implant Innovations, Inc., Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/174,188

(22) Filed: Jun. 18, 2002

(65) Prior Publication Data

US 2002/0151423 A1 Oct. 17, 2002

Related U.S. Application Data

(60) Continuation of application No. 10/014,375, filed on Oct. 26, 2001, now Pat. No. 6,413,000, which is a division of application No. 09/525,573, filed on Mar. 15, 2000, now Pat. No. 6,325,750.
(60) Provisional application No. 60/124,385, filed on Mar. 15, 1999.

(51) Int. Cl.[7] .................................................. B04B 5/02
(52) U.S. Cl. .............................. 494/21; 494/26; 383/40; 383/904; 604/410
(58) Field of Search .............................. 494/20, 21, 23, 494/25, 26, 31–33, 45; 210/109, 512.1, 781, 782; 141/114, 313; 222/214; 604/408, 410; 383/9, 38, 40, 904

(56) References Cited

U.S. PATENT DOCUMENTS

| | | | |
|---|---|---|---|
| 3,211,368 A | * | 10/1965 | Shanley |
| 4,119,407 A | * | 10/1978 | Goldstein et al. |
| 4,439,177 A | * | 3/1984 | Conway |
| 4,447,220 A | | 5/1984 | Eberle |
| 4,482,342 A | * | 11/1984 | Lueptow et al. |
| 4,576,603 A | * | 3/1986 | Moss |
| 4,892,668 A | * | 1/1990 | Harmony et al. |
| 5,092,996 A | * | 3/1992 | Spielberg |
| 5,318,556 A | * | 6/1994 | Avallone et al. |
| 5,456,845 A | * | 10/1995 | Nishimura et al. |
| 5,549,540 A | * | 8/1996 | Moore et al. |
| 5,858,253 A | | 1/1999 | Holm |
| 6,071,421 A | * | 6/2000 | Brown |

FOREIGN PATENT DOCUMENTS

| | | |
|---|---|---|
| DE | 44 45 030 A1 | 6/1996 |
| DE | 197 01 263 A1 | 7/1998 |
| WO | WO 91/17778 | 11/1991 |
| WO | WO 92/00145 | 1/1992 |

OTHER PUBLICATIONS

American Association of Blood Bank's Technical Manual, 12th Edition, 1996, pp. 700–701, 716.*

* cited by examiner

*Primary Examiner*—Charles E. Cooley
(74) *Attorney, Agent, or Firm*—Jenkens & Gilchrist

(57) ABSTRACT

A single use system and kit for producing blood platelet concentrates is described herein. In a preferred form, the kit includes a bag set in which compartments containing blood components are adjacent to to separate compartments which can be inflated to express the blood components after their separation by centrifuging.

7 Claims, 6 Drawing Sheets

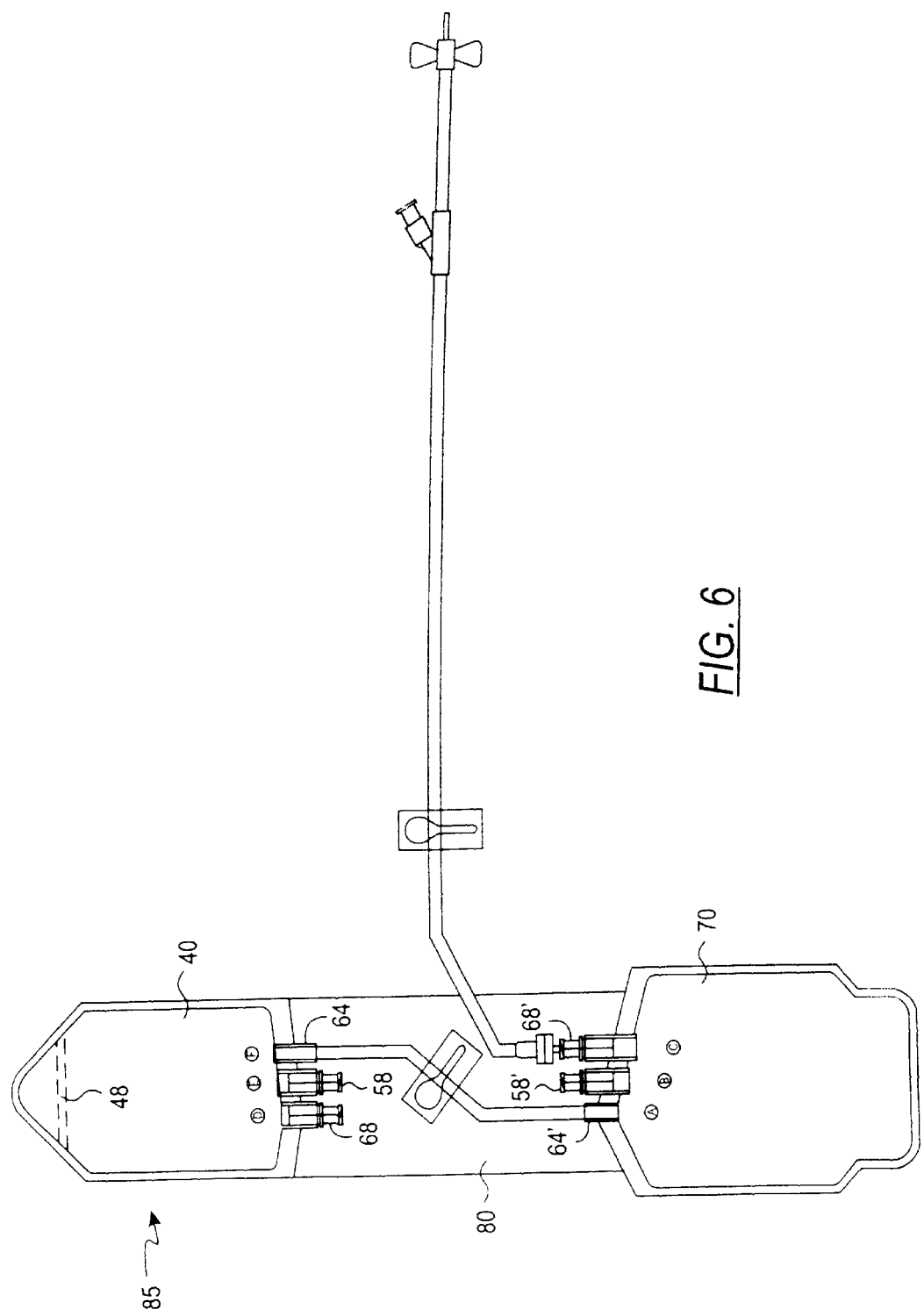

PLATELET COLLECTION SYSTEM

This is a continuation of U.S. Ser. No. 10/014,375, filed Oct. 26, 2001, now U.S. Pat. No. 6,413,000, which is a division of U.S. Ser. No. 09/525,573, filed Mar. 15, 2000, now U.S. Pat. No. 6,325,750, which claimed benefit of provisional application 60/124,385, filed Mar. 15, 1999.

TECHNICAL FIELD OF THE INVENTION

This invention relates to processing whole blood into platelet-rich plasma and, more particularly, to improvements in blood processing systems for generating platelet-rich plasma from autologous blood.

BACKGROUND OF THE INVENTION

The science and effectiveness of using platelet-rich plasma derived from the patient's own blood in surgery are documented in medical, trade and science journals. A known method for the preparation of platelets from whole blood is described in the American Association of Blood Bank's Technical Manual, 12th Edition, 1996, at pages 700–701, Method 9.11. A system employing this method collects the patient's whole blood into a collection unit with two integrally-attached transfer containers. The blood is collected into the collecting container, the other two transfer containers are collapsed, and the two transfer containers with the collecting container are subjected to a "soft spin" in a centrifuge, which brings the plasma to the top of the collecting unit, leaving red cells at the bottom. In the next step, the collecting container containing the blood is squeezed in a plasma extractor to force the platelet-rich plasma into one of the transfer containers through a connecting tube. A fraction comprising red cells remains behind in the collecting container, which is then removed. Next, the two transfer containers, the first being empty and the second containing the plasma, are subjected to a "heavy spin" in a centrifuge to concentrate platelets at the "bottom" of the second transfer container, leaving a platelet-poor fraction of the plasma (PPP) above the platelet concentrate (PC) in the second transfer container. The following step squeezes the second transfer container to express the PPP into the first transfer container. The platelet concentrate (PC) is then resuspended and collected for use. This system uses a process requiring six separate steps, including two centrifugal steps and two separation steps. The terms "light spin" and "heavy spin" are defined in Table 10.5-1 at page 716 of the AABB Technical Manual.

SUMMARY OF THE INVENTION

It is an object of this invention to provide a single use system for producing platelet concentrates (PC). Preferably, the system is in the form of a kit including disposable components supplied sterile in disposable packaging, and having all of the components required to draw blood from the patient, prevent blood coagulation, process the sample into platelet concentrate, and deliver the platelet concentrate to a surgical site. It is a particular object of the invention to provide such a system that will be useful to medical and dental practitioners, including, but not limited to, dentists, periodontists, and oral and maxillofacial surgeons.

The invention in one of its aspects provides a bag set comprising two bags joined by a tube which includes a built-in sample site at the second bag and has sloped top surface geometry at both bags for improved and more efficient cell separation and collection. This new bag set may be pre-charged with an anticoagulant. A preferred size range is 50–100 ml, but the invention is not limited to any particular size range.

In another aspect of the invention, each bag consists of two compartments, the first for the sedimentation of cellular material and the second to serve as an inflatable device for the purpose of expressing supernatant liquid from the first compartment.

In still another aspect, the invention provides a bifurcated centrifuge bucket having two wells, into each of which one of the cell bags is placed together with an inflatable device, and a means successively to inflate each inflatable device to perform each expression step following the soft spin and the heavy spin, thereby eliminating the step of removing the bag set from the bucket after each spin. In a further aspect, the invention provides means to express the supernatant liquid from within the bucket, thereby eliminating the need to remove the bag set from the bucket after the heavy spin.

BRIEF DESCRIPTION OF THE DRAWINGS

The invention is disclosed in greater detail with reference to the accompanying drawings.

FIG. 5a is a schematic side view of the two chamber bag.

FIG. 5b is a sectional edge view of the bag of FIG. 5a.

FIG. 5c is a top sectional view showing the tubulations which provide access to the bag of FIG. 5a.

FIG. 6 is a plan view of a unitary two bag set.

DESCRIPTION OF ILLUSTRATIVE EMBODIMENTS

FIGS. 1–4 illustrate the principles by which bags of the invention operate. FIGS. 5–9 illustrate preferred embodiments.

Figure 1:
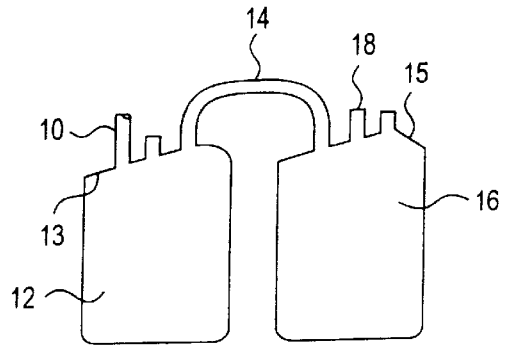
FIG. 1 illustrates a set of two bags according to the invention.
Figure 3:
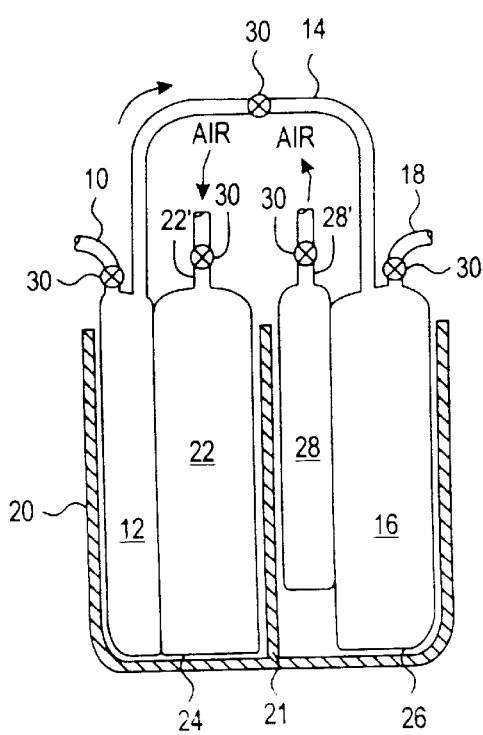
FIG. 3 illustrates the third bag being inflated.
Figure 4:
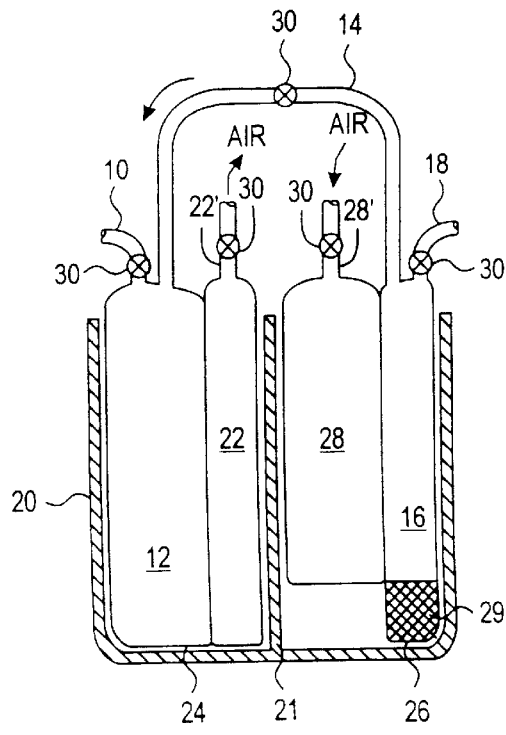
FIG. 4 illustrates the fourth bag being inflated.

In FIG. 1, a standard needle set (not shown) may be coupled via access tube 10 to a first bag 12 which is connected via a transfer tube 14 to a second bag 16. A sample site is provided at an access tube 18 fitted to the second bag. The top wall 13, 15 of each bag may be sloped as shown for more efficient cell separation and collection. The principles on which invention operates are schematically illustrated in FIGS. 2–4.

Figure 2:
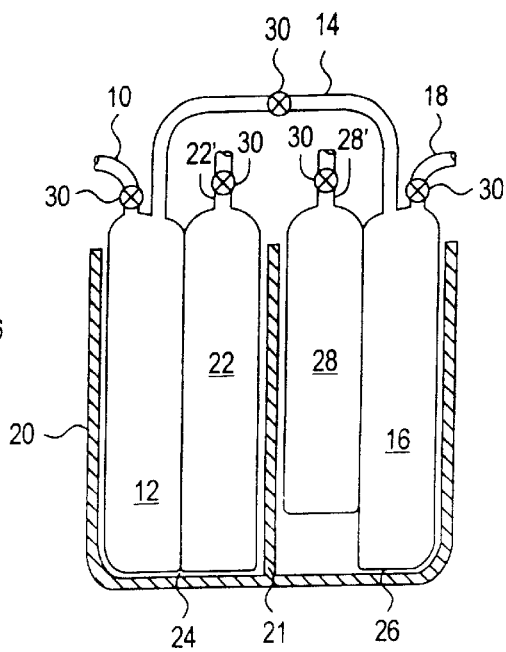
FIG. 2 shows the bag set in a bifurcated centrifuge bucket with adjacent inflatable third and fourth respective bags.

In FIG. 2, the bag set 12, 16 is shown in a bifurcated centrifuge bucket 20 having two wells 24, 26 separated by a partition 21. Each cell bag 12, 16 is in one of the respective wells 24, 26 together with a third or fourth inflatable bag 22, 28, respectively, which is not connected to the interior of the associated cell bag. The transfer tube 14 connects the interior of the two cell bags 12, 16. Each inflatable bag has an access tube 22', 28', respectively. Each of the access tubes, 10, 18, 22' and 28' may be furnished with a valve 30 to control access to the interior of the respective bags. Transfer tube 14 may also be provided with a valve 30, as shown, to isolate the cell bags during centrifugation. The fourth inflatable bag 28 is shorter than its companion cell bag 16, so that a desired volume (e.g., about 5 ml) of plasma concentrate will be left in bag 16 when bag 28 is inflated to a desired pressure.

In use, the first bag 12 is charged with the patient's blood sample in preparation for the soft spin. The inflatable bags 22 and 28 are not inflated. The contents of the bucket 20 are then subjected to a soft spin as described above. After the soft spin, as shown in FIG. 3, a pump (not shown) or other air source is connected via the access tube 22' to the third bag 22 and the third bag is inflated, squeezing the first bag 12 and forcing the plasma fraction over the transfer tube 14 into the second bag 16, leaving the red cell fraction behind in the first bag. The contents of the bucket 20 are then subjected to a heavy spin, as described above. The third bag may be left inflated during centrifuging of the bucket and its contents. Following the heavy spin, the contents of the second bag 16 are a pellet of platelet concentrate 29 (see FIG. 4) at the bottom of the bag and platelet-poor plasma above the platelet concentrate. A pump (not shown) or other air source may be attached to the access tube 28' of the smaller fourth bag 28, and that bag is inflated and platelet-poor plasma may be forced into the first bag 12 via the transfer tube 14, as shown in FIG. 4. Expression is continued until the platelet poor plasma above the platelet concentrate is expressed into first bag 12, leaving the platelet rich plasma in the second bag 16. With this new arrangement of the invention, the platelet concentrate fraction is processed into the second bag 16 without a need to remove the bags from the centrifuge bucket during the process. Further according to the invention, the platelet concentrate can be removed from the second bag 16 via the sample site tube 18 using a known extraction syringe.

Figure 5B:
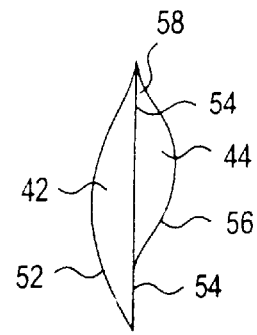
Figure 5C:
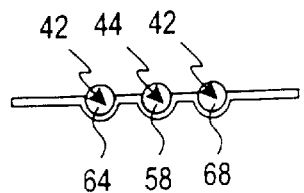
Figure 5A:
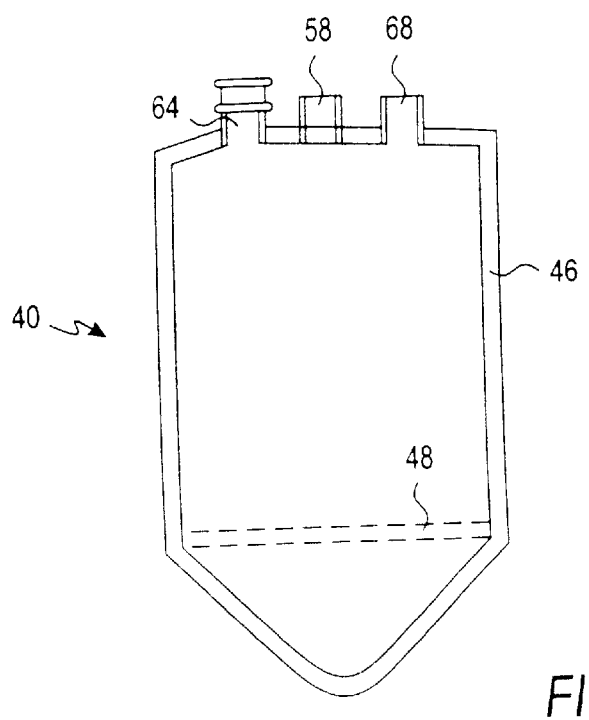
FIGS. 5a, b and c illustrate a two chamber bag.

FIGS. 5a, 5b and 5c illustrate a two chamber bag 40 which combines a collection chamber 42 and an expression chamber 44 in a single structure. This bag 40 corresponds to bags 16 and 28 in FIGS. 2–4. In the edge view shown in FIG. 5b, three sheets 52, 54 and 56 are joined at their peripheries with a weld seam 46 (see FIG. 5a). Typically, the sheets will be of a flexible plastic. The outer sheets 52 and 56 are shown expanded for clarity. In addition, for use of the collection chamber 42 for platelet collection (e.g., bag 16 in FIG. 1), a second weld seam 48 joins the intermediate sheet 54 to the expression chamber sheet 56 to shorten the expression chamber so as to isolate the desired volume of platelet concentrate with the PC produced by the invention. FIG. 5b illustrates the effect of inflating the expression chamber 44. A similar two chamber structure 70 (see FIG. 6), without the second weld seam 48, is the equivalent of the first bag 12 and its associated expression device 22 shown in FIGS. 2–4.

As shown in FIG. 5a, tubulations 58, 64 and 68 are provided in this integrated structure 40 for providing access to the chambers 42 and 44 (FIG. 5b). The first tubulation 58 is sealed between the sheets 54 and 56 defining the expression cavity 44, and provides access corresponding to the access tube 28' leading into the inflatable bag 28 in FIG. 2. The second tubulation 64 is sealed between the sheets 52 and 54 defining the platelet collection chamber 42, and provides access for a transfer tube (e.g., tube 14 in FIG. 1). The third tubulation 68 is similarly provided into the collection chamber, and provides access corresponding to the sample site tube 18 in FIG. 1. A top view, FIG. 5c, further illustrates the tubulations 58, 64 and 68, providing access to expression cavity 44 and collection chamber 42 of FIG. 5b.

Figure 9:
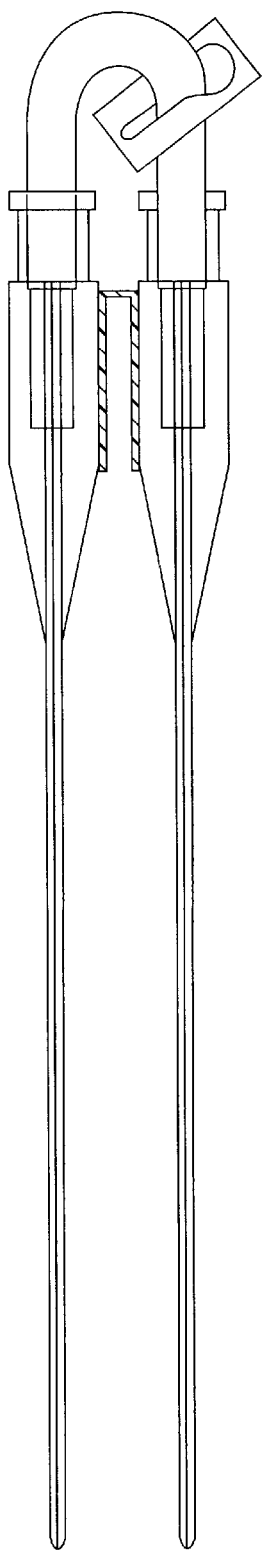
FIG. 9 illustrates a two bag set attached to a rigid u-shaped bridge.

FIG. 6 shows a pair of two chamber structures 40, 70 that may be joined by an optional bridge 80 between their respective ends that are fitted with tubulations (58, 64 and 68 for structure 40 and $58_1$, $64_1$ and $68_1$ for structure 70) to constitute the bag set 85. The bridge may also be omitted. As shown, structure 40 includes platelet collection chamber 42 (FIG. 5b) corresponding to bag 16 in FIGS. 2–4 (facing upward) and expression cavity 44 (FIG. 5b) corresponding to bag 28 in FIGS. 2–4 (facing downward). Structure 70 includes a collection chamber corresponding to bag 12 in FIGS. 2–4 (facing upward) and an expression cavity (facing downward) corresponding to bag 22 in FIGS. 2–4. The tubulations 58, 64 and 68 shown in FIG. 5 are shown in FIG. 6, with the corresponding tabulations $58_1$, $64_1$ and $68_1$ associated with structure 70. In use, this bag set is placed in the bifurcated bucket 20 (FIGS. 2–4), with the structure 70 corresponding to cell bag 12 in well 24, and the structure 40 corresponding to cell bag 16 in well 26. The optional bridge 80 may be flexible or rigid but, in either case, it would contact partition 21 (FIGS. 2–4) with the pairs of bags on the desired side of the centrifuge bucket. As shown, the bridge is flexible and may be a part of the two chamber structures. Alternatively, the bridge could be a relatively rigid plastic molded in a U-shape to fit over the partition 21 as illustrated in FIG. 9.

Figure 7:
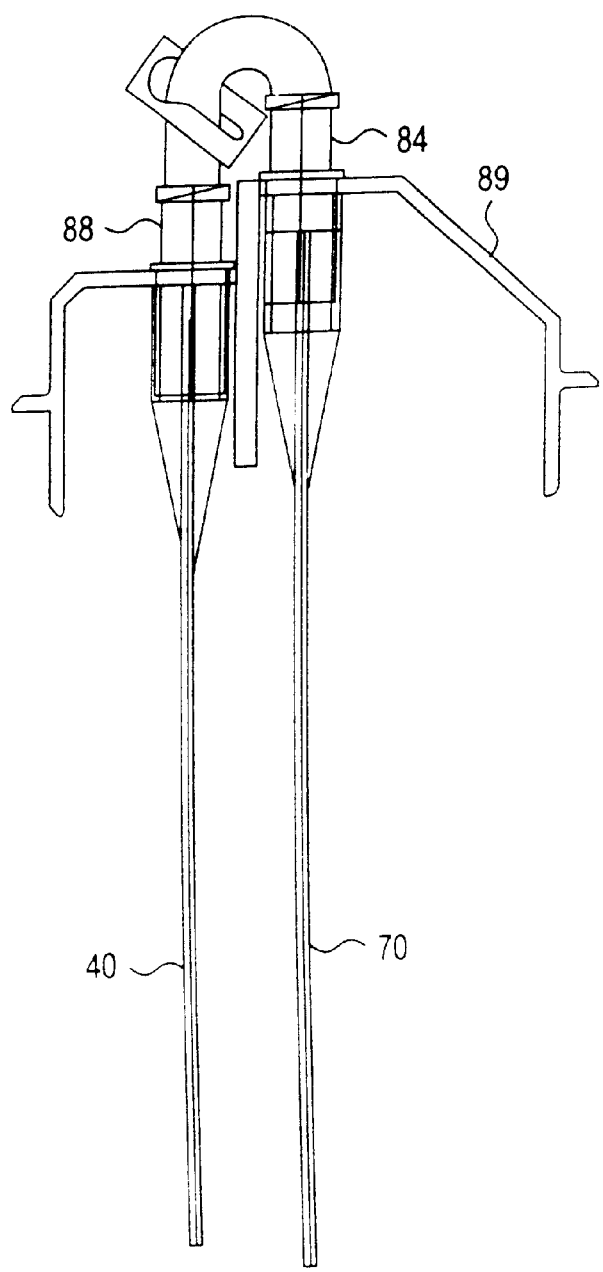
FIG. 7 illustrates the bag set of FIG. 6 assembled to a supporting cover for the centrifuge bucket.
Figure 8:
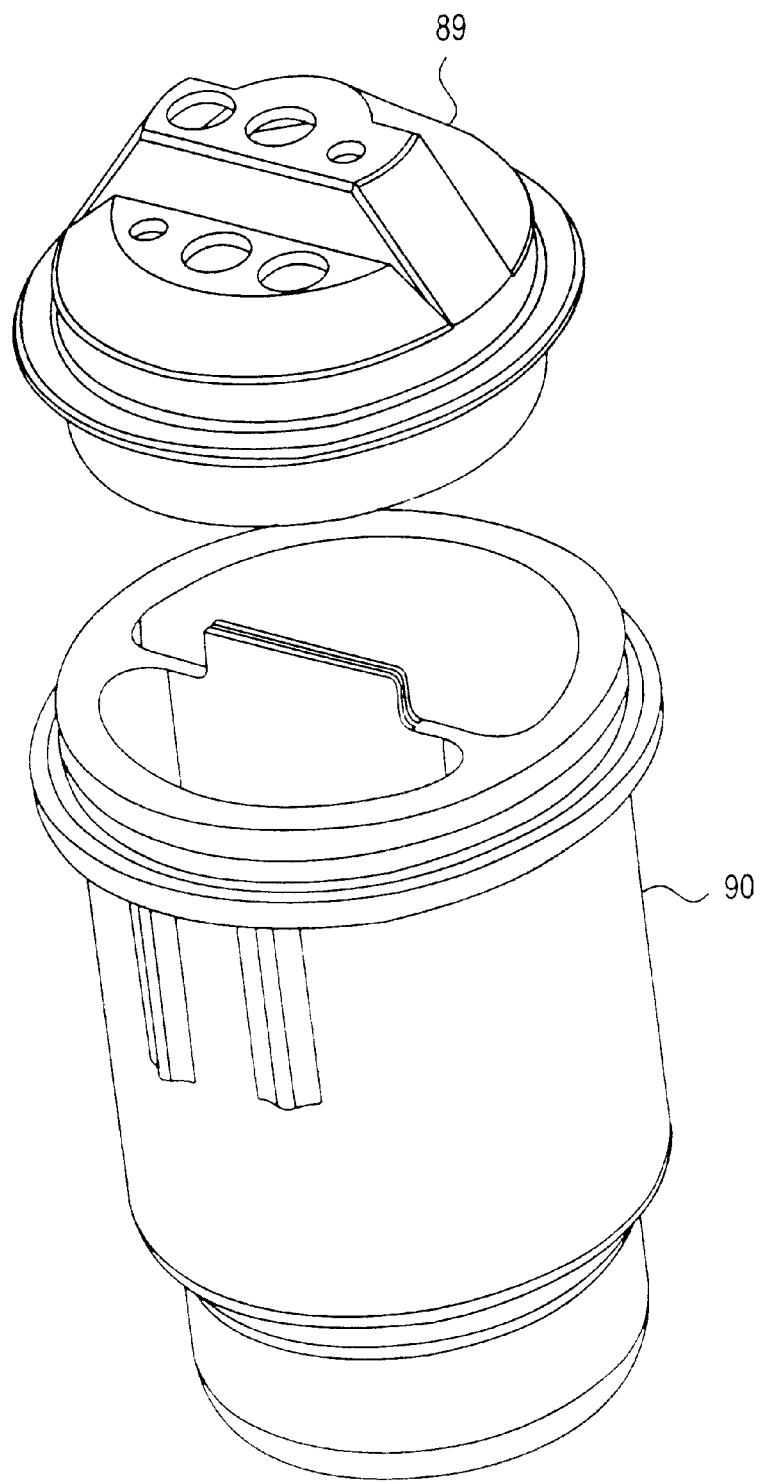
FIG. 8 is an isometric view of a centrifuge bucket.

The installation of the bag set 85 in a supporting cover 89, ready for installation in a bifurcated bucket (20 in FIGS. 2–4 and 90 in FIG. 8) is shown in FIGS. 7–8. In FIG. 7, the assembled bags are shown as they would be seen if 40 and 70 of FIG. 6 were folded at the middle and viewed from the side of FIG. 6. The larger two chamber structure 70 is at the right of the drawing, and the smaller two chamber structure 40, used to collect the PC product, is at the left in FIG. 7. The tubulations provided for access to the bags that contain blood or blood products may be fitted with valves 84, 88. These valves have sufficient mass to require restraint against moving into the wells 24, 26 (see FIGS. 2–4) under centrifugal force, and supporting cover 89 is provided to support and restrain them against such movement and to facilitate making and breaking connections to the valves.

Supporting cover 89 is shown in FIG. 8 without the two chamber structures 40 and 70 of FIG. 7. In FIG. 8, it can be seen that the supporting cover 89 is intended to seat on the centrifuge bucket 90. The two chamber structures 40 and 70 will be inserted into the two sides of the centrifuge bucket, where they will be used according to the procedure described connection with FIGS. 2–4. The centrifuge bucket will typically be made of a plastic, which may be clear or translucent to facilitate observation of the processing of blood into its components as described above.

What is claimed is:

1. A pair of compartmented containers for use in separating blood into component red cells, platelet-poor plasma, and platelet concentrate comprising two integrated structures, each of said structures consisting of three flexible sheets sealed at the edges to form a first cavity and a second cavity, each of the first cavities adapted to hold blood components and each of the second cavities adapted to receive air under pressure, said integrated structures having tubulations to provide access to the interior of said cavities, the interiors of the first cavities being connected together by a hollow tubing extending between said tubulations, said second cavities adapted to expand under pressure to compress respective said first cavities in order to expel contents therefrom, said pair of integrated structures being adapted to fit within a centrifuge bucket having an internal wall for separating said integrated structures, wherein one of said integrated structures has a weld seam joining one of said flexible sheets to an intermediate flexible sheet to shorten the second cavity formed between said sheets.

2. A pair of compartmented containers of claim 1, wherein at least one of said compartmented containers has a sloped top edge adjacent said tubulations to provide efficient collection and separation of blood components.

3. A pair of compartmented containers of claim 1, wherein said containers are connected to a rigid u-shaped bridge adapted to contact said internal wall of said centrifuge bucket.

4. A blood platelet collection system comprising:
   a. a centrifuge bucket having an internal partition defining two wells therein;
   b. a pair of compartmented containers for use in separating blood into component red cells, platelet-poor plasma, and platelet concentrate comprising two integrated structures, each of said structures consisting of three flexible sheets sealed at the edges to form a first cavity and a second cavity, each of the first cavities adapted to hold blood components and each of the second cavities adapted to receive air under pressure, said integrated structures having tubulations to provide access to the interior of said cavities, the interiors of the first cavities being connected together by a hollow tubing extending between said tubulations, said second cavities adapted to expand under pressure to compress respective said first cavities in order to expel contents therefrom, each of said integrated structures being adapted to fit within a respective well of said centrifuge bucket;
   c. a cover for said centrifuge bucket providing access to said tubulations and for restraining valves connected to said tubulations against centrifuged force.

5. A blood platelet collection system of claim 4 wherein one of said integrated structures has a weld seam joining one of said flexible sheets to an intermediate flexible sheet to shorten the second cavity formed between said sheets.

6. A blood platelet collection system of claim 4 wherein at least one of said compartmented containers has a sloped top edge adjacent said tubulations to provide efficient collection and separation of blood components.

7. A blood platelet collection system of claim 4 wherein said compartmented containers are connected to a rigid u-shaped bridge adapted to contact said internal partition of said centrifuge bucket.

* * * * *